(12) United States Patent
Kulkarni et al.

(10) Patent No.: US 9,150,497 B2
(45) Date of Patent: Oct. 6, 2015

(54) CONTINUOUS TWO STEP FLOW SYNTHESIS OF M-AMINO ACETOPHENONE

(71) Applicant: COUNCIL OF SCIENTIFIC & INDUSTRIAL RESEARCH, New Delhi (IN)

(72) Inventors: Amol Arvind Kulkarni, Maharashtra (IN); Ramesh Anna Joshi, Maharashtra (IN); Rohini Ramesh Joshi, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/351,791

(22) PCT Filed: Oct. 15, 2012

(86) PCT No.: PCT/IB2012/002052
§ 371 (c)(1),
(2) Date: Apr. 14, 2014

(87) PCT Pub. No.: WO2013/054181
PCT Pub. Date: Apr. 18, 2013

(65) Prior Publication Data
US 2014/0243556 A1    Aug. 28, 2014

(30) Foreign Application Priority Data
Oct. 14, 2011 (IN) .......................... 2956/DEL/2011

(51) Int. Cl.
*C07C 209/00* (2006.01)
*C07C 221/00* (2006.01)
*C07C 201/08* (2006.01)

(52) U.S. Cl.
CPC ............. *C07C 221/00* (2013.01); *C07C 201/08* (2013.01)

(58) Field of Classification Search
None
See application file for complete search history.

(56) References Cited

FOREIGN PATENT DOCUMENTS

JP            05246957 A    *    9/1993

OTHER PUBLICATIONS

King et al, Journal of American Chemical Society, 1945, 67, 2089-92.*

* cited by examiner

*Primary Examiner* — Sudhakar Katakam
(74) *Attorney, Agent, or Firm* — McDonnell Boehnen Hulbert & Berghoff LLP

(57) ABSTRACT

Disclosed herein is a continuous tubular reactor based conversion of acetophenones to amino substituted acetophenones wherein the nitration is carried out at −10 to 10° C. followed by reduction to m-nitrophenone resulting in uniform output of product, said process comprising the steps of: a) Nitrating acetophenone with nitrating agent (nitration mixture or fuming nitric acid) at −10 to 10° C.; b) Isolating m-nitro acetophenone from a mixture of o and m-nitro acetophenone and c) Reducing the m-nitro to obtain m-amino acetophenone.

7 Claims, 2 Drawing Sheets

CONTINUOUS TWO STEP FLOW SYNTHESIS OF M-AMINO ACETOPHENONE

This application is a US national phase of International Application No. PCT/IB2012/002052 filed on Oct. 15, 2012, which claims priority to Indian Patent Application No. 2956/DEL/2011 filed on Oct. 14, 2011, the disclosures of which are incorporated herein by reference in their entirety.

The following specification particularly describes and ascertains the nature of this invention and the manner in which it is to be performed:

TECHNICAL FIELD

This invention relates to continuous process for synthesis of m-Amino Acetophenone using tubular reactor. The invention more particularly relates to continuous two step flow synthesis of m-Amino Acetophenone.

BACKGROUND AND PRIOR ART

The nitro derivatives of aromatic compound find applications in the manufacture of dyes, API's, pesticides and fine chemicals. Typically the exothermic nature of nitration of aromatic substrates does not facilitate an easy scale-up based on laboratory experiments and more precautions are taken to make the entire process safer with larger scales. Also, as it is mentioned in the analysis of industrial and laboratory nitration processes (ACS Symposium Series, 22, ACS, 1976, 201) in general the aromatic nitration is a heterogeneous system and the rate of nitration strongly depends upon the interfacial mass transfer rates and the nature of dispersion. Relative rates of mass transfer and the rate of parallel reactions affect the overall conversion as well as the selectivity of a specific isomer. Thus providing adequate heat transfer area to take care of the heat duty and provide efficient mixing to enable high diffusion rates is essential for the scale-up of nitration processes. While some of these constraints are observed while doing nitration in batch or semi-batch mode, they can be overcome effectively in continuous mode of operation.

Continuous flow nitration of organic substrates has been reported in a few patents U.S. Pat. No. 4,091,042 and U.S. Pat. No. 4,021,498 discuss the continuous adiabatic nitration of nitrobenzene. EP0436443B1 covers a continuous process for nitration of nitratable organic substrates including hydrocarbons and halogenated aromatic hydrocarbons. More recently, the patent (WO2007087816A1) based on. Corning's Advanced Flow reactor on nitration of aromatic substrates demonstrates the ability of the specific device towards nitration of a few organic and specifically aromatic substrates.

OBJECTIVE OF THE INVENTION

The main objective of the present invention is to provide a continuous process for synthesis of m-Amino Acetophenone using tubular reactor.

Another objective of the present invention is to provide a continuous two step flow synthesis of m-Amino Acetophenone.

Another objective of the present invention is to provide an efficient method to continuously synthesize m-nitroacetophenone and its reduced derivative, m-aminoacetophenone with 98% yield and 100% purity in the reduction step.

SUMMARY OF INVENTION

Accordingly, the present invention provides a continuous method of conversion of acetophenones to amino substituted acetophenones using tubular reactor wherein the nitration is carried out at 0-10° C. followed by reduction to m-nitrophenone resulting in uniform output of product, said process comprising the steps of:
 a) nitration of acetophenone with nitration mixture at 0-10° C.;
 b) nitration of acetophenone with fuming nitric acid at −10-20° C.
 c) Isolating the m-nitro acetophenone from a mixture of o and m-nitro acetophenone by quenching of the reaction in ice and extraction in an organic solvent,
 d) reduction the m-nitro acetophenone to obtain m-amino acetophenone.

In an embodiment of the invention, the acetophenone can be dissolved in sulfuric acid prior to subjecting to nitration process.

In an embodiment of the invention, the ratio of acetophenone to sulfuric acid can be 1:0 to 1:2.5 w/v.

In yet another embodiment, the ratio of substrate mixture to nitrating mixture is 1:1.66 v/v.

In yet another embodiment, reducing agent is selected from the group consisting of $SnCl_2$ and $Na2S$.

In yet another embodiment, organic solvent used is selected from the group consisting of toluene and diethyl ether.

In yet another embodiment, the nitration mixture is standard nitrating mixture.

In yet another embodiment, the nitrating agent is fuming nitric acid.

DETAILED DESCRIPTION OF THE INVENTION

Figure 1:
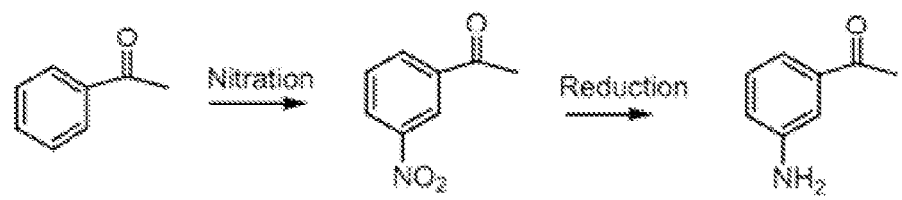
FIG. 1: Synthesis of m-aminoacetophenone from acetophenone

The present invention provides a continuous flow process for the nitration of acetophenone using nitrating mixture as well as using fuming nitric acid alone to yield 3-nitro acetophenone. The process involves the following:

(i) Nitration with nitrating mixture:
 a. Dissolution of acetophenone in sulfuric acid when nitrating agent is the nitrating mixture (sulfuric acid and nitric acid) such that the acetophenone stream is maintained above its melting point while the sulfuric acid is chilled between 0 to 4° C.
 b. Mixing of acetophenone solution in sulfuric acid with the nitric acid (70%) at constant temperature using a micromixer.
 c. Letting the reaction mixture to flow through a plain pipe or a microreactor immersed in a constant temperature bath till the reaction is complete achieving almost complete conversion of acetophenone and specific isomers subject the reactor temperature and the residence time.
 d. The reaction is quenched continuously by adding ice-chilled water inline at the end of the reactor to the reaction mixture and collect the dilute reaction stream on ice.

(ii) Nitration with fuming nitric acid
 a. Mixing of acetophenone with fuming sulfuric acid using a micromixer such that the acetophenone stream is maintained above its melting point while the sulfuric acid is chilled between −10 to 10° C.
 b. Letting the reaction mixture to flow through a plain pipe or a microreactor immersed in a constant temperature bath till the reaction is complete achieving almost complete conversion of acetophenone and specific isomers subject the reactor temperature and the residence time.
 c. The reaction is quenched continuously by adding ice-chilled water inline at the end of the reactor to the reaction mixture and collect the dilute reaction stream on ice.

Reduction of m-nitro acetophenone was achieved by mixing of m-nitroacetophenone with a solution of reducing agent in ethanol, which leads to the formation of m-amino acetophenone.

The conventional route for the manufacture of 3-nitroacetophenone is nitration of acetophenone using nitrating mixture. The reaction is extremely exothermic and needs to be carried out at 5° C. with controlled addition of acetophenone over several hours. The addition time period is crucial because if the additions over longer time leads to the decomposition of raw material giving a poor yield. Also, very efficient stirring is also required to get reasonable yields (Org. Syn. Coll. Vol. 2, 434, 1943.)

The reduced derivative of m-nitroacetophenone i.e. 3-aminoacetophenone is an important raw material used for the synthesis of m-hydroxy acetophenone used as an API for Rivastigmine which is a drug use for the treatment of mild to moderate dementia of the Alzheimer's type and dementia due to Parkinson's disease. The current methods available for the synthesis of m-aminoacetophenone is a prolonged reaction that is carried out at very low temperatures.

In view of the above, there is a need in the art to provide a continuous process for the synthesis of m-nitroacetophenone and its reduced derivative, m-aminoacetophenone that can be easily scalable without compromising on yields and purity.

In continuation with our efforts to meet above objective, the study of the nitration of reactive aromatic substrates, particularly, the nitration of acetophenone is taken up in the microreactor system. According to the invention, the focus of the study was limited to the first two steps of the synthesis as shown in FIG. 1.

In the first step of nitration, the literature reports indicate that second order kinetics apply for this reaction and the rate constant decreases with increase in the concentration of nitric acid, thus lowering the role of nitric acid in this process. The reaction rates strongly depend upon the concentration of substrate and the concentration of nitronium ions generated in the reaction which largely depends on the amount of sulfuric acid present. Importantly, the presence of sulfuric acid is necessary even to activate the organic substrate for nitration reaction thereby helping to accelerate the reaction.

The existing batch method is transformed to continuous mode using micromixers and tubular reactors. The reaction conditions have been improved to achieve the desired yield of the desired isomer from the nitration reaction. Currently, there is no known continuous flow synthesis process for meta aminoacetophenone. The key added advantage is making both the steps continuous and mainly to achieve consistent product yield, wherein the nitration is carried out at 5° C. instead of cryogenic temperatures (−10° C.) without affecting the yield.

The invention discloses a continuous tubular reactor based conversion of acetophenones to amino substituted acetophenones wherein the nitration is carried out at 0-10° C. followed by reduction to m-nitrophenone resulting in uniform output of product, said process comprising the steps of:
 a) Nitrating acetophenone with nitration mixture at 0-10° C.;
 b) Isolating the m-nitro acetophenone from a mixture of o and m-nitro acetophenone by quenching of the reaction in ice and extraction in an organic solvent and
 c) Reducing the m-nitro to obtain m-amino acetophenone.

The acetophenone either is dissolved in sulfuric acid in the ratio of acetophenone to sulfuric acid 1:2.5 w/v, prior to subjecting to nitration process or used neat.

The ratio of substrate mixture to nitrating mixture may be in the ratio of 1:1.66 v/v.

The process according to the invention results in uniformity of output i.e. the variation in product is as little as ±1%. The invention can be broadened to various substrates having different groups to yield corresponding m-amino phenones.

In the preferred embodiment, the invention provides continuous process for the synthesis of m-nitroacetophenone and its reduced derivative using microreactor system as shown below in FIG. 2 and FIG. 3.

Figure 3:
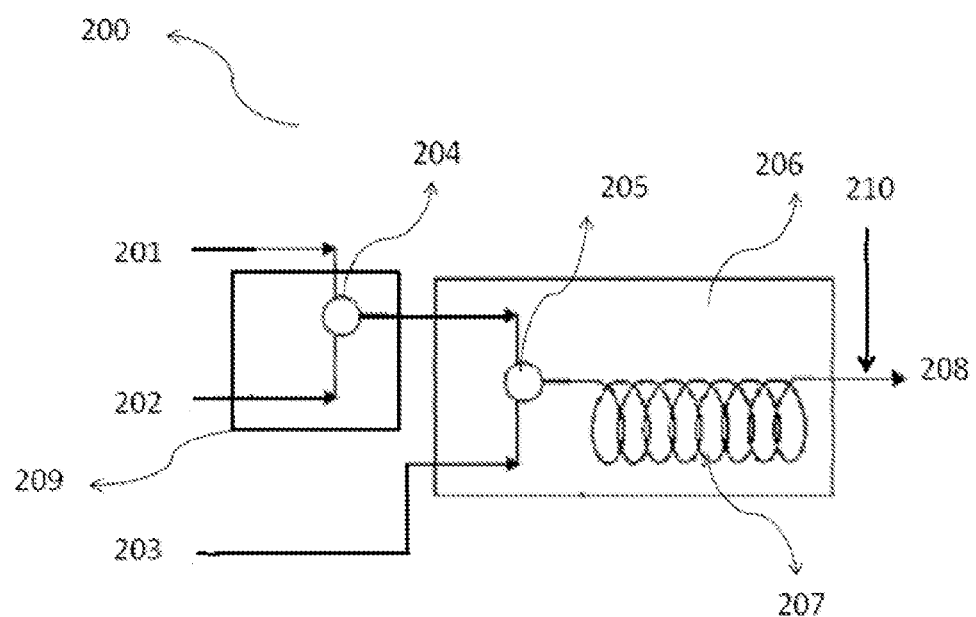
FIG. 3: Schematic of the experimental set-up (200) having: (201) inlet stream for acetophenone, (202) inlet stream for sulfuric acid, (203) inlet stream for nitric acid, (204 and 205): Micromixers, (206) constant temperature bath, (207) continuous reactor, (208) outlet stream, (209) constant temperature bath for cooling (202) and mixing of streams (201) and (202), (210) chilled water stream for quenching. One approach of the process according to the invention includes preparation of acetophenone and nitration mixture (FIG. 2). Tubular reactor was used in coil or serpentine form or their combinations in the same form or in microfabricated microchannels. In all the cases, flow rates were adjusted to achieve the desired residence time. Suitable micromixer was used for mixing of reactants before they enter the continuous reactor (tubular or its variants). The reaction is quenched continuously by adding ice-chilled water inline at the end of the reactor to the reaction mixture and collect the dilute reaction stream on ice. The samples were collected on crushed ice and the product was filtered and washed twice with ice cold water. Then residue was dried for an hour and the filtrate was extracted by using organic solvent (viz. diethyl ether).

In another approach of the process according to the invention includes use of acetophenone, sulfuric acid and nitric acid (FIG. 3). Acetophenone and sulfuric acid were mixed continuously and then the mixture was brought in contact with nitric acid through another micromixer. Tubular reactor was used in coil or serpentine form or their combinations in the same form or in microfabricated microchannels. In all the cases, flow rates were adjusted to achieve the desired residence time. Suitable micromixer was used for mixing of reactants before they enter the continuous reactor (tubular or its variants). The reaction is quenched continuously by adding ice-chilled water inline at the end of the reactor to the reaction mixture and collect the dilute reaction stream on ice. The samples were collected on crushed ice and the product was filtered and washed twice with ice cold water. Then residue was dried for an hour and the filtrate was extracted by using organic solvent (viz. diethyl ether).

Figure 2:
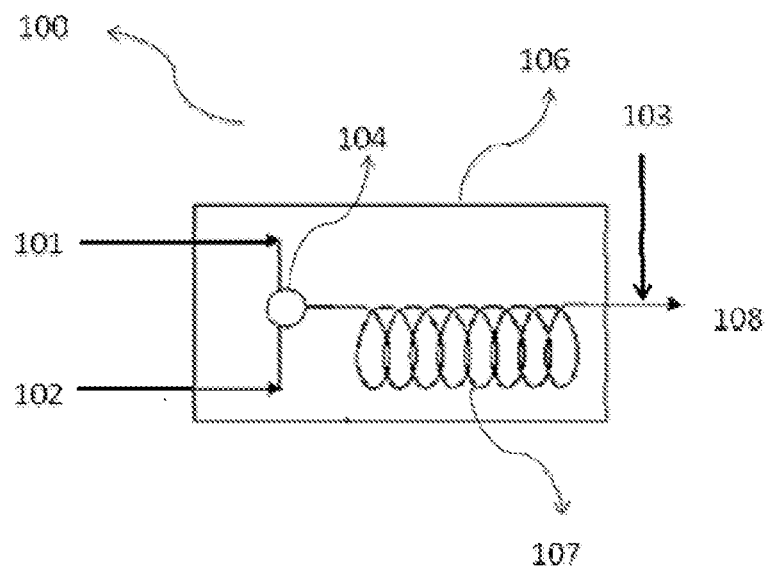
FIG. 2: Schematic of the experimental set-up (100) having: (201) inlet stream for acetophenone (or separately prepared mixture of acetophenone in sulfuric acid), (102) inlet stream for fuming nitric acid (or concentrated nitric acid), (104) Micromixer, (106) constant temperature bath, (107) continuous reactor, (108) outlet stream, (103) chilled water stream for quenching.

In another approach of the process according to the invention includes use of neat acetophenone and fuming nitric acid (FIG. 2). Tubular reactor was used in coil or serpentine form or their combinations in the same form or in microfabricated microchannels. In all the cases, flow rates were adjusted to achieve the desired residence time. Suitable micromixer was used for mixing of reactants before they enter the continuous reactor (tubular or its variants). The reaction is quenched continuously by adding ice-chilled water inline at the end of the reactor to the reaction mixture and collect the dilute reaction stream on ice. The samples were collected on crushed ice and the product was filtered and washed twice with ice cold water. Then residue was dried for an hour and the filtrate was extracted by using organic solvent (viz. diethyl ether).

In another preferred embodiment, the reduction reaction of meta nitro acetophenone was carried out in metallic or non-metallic continuous reactor (stirred or tubular) using a suitable reducing agent (viz. $SnCl_2$, $Na2S$, etc.). The reaction was seen to be complete with only the product being observed at the outlet. No separate quenching was required.

The invention has significant importance as it forms the basis for converting the existing batch processes for meta amino acetophenone and subsequent diazotization to continuous mode with better control on the product profile. This invention will help achieve a safe and improved process for the synthesis of meta aminoacetophenone.

The following examples are given by way of illustration and should not be construed to limit the scope of invention.

EXAMPLES

The experiments were performed in two steps, as per the FIG. 1. Individual steps were studied separately and were further used for integration. In both the stages, batch as well as continuous flow experiments were performed and later optimized for the highest yield at lab scale. The details of the experimental procedure are given as follows.

Example 1

Experimental Set-Up and Experimental Procedure

Preparation of Solutions:
A solution of acetophenone in concentrated sulfuric acid was prepared in a beaker in ice-salt bath at a temperature between −5 to 0° C. The addition of acetophenone to sulfuric acid was done drop wise such that the mixture temperature does not rise above 2° C. Because of the low melting point of acetophenone (19° C.), during the addition it was kept at room temperature to retain it in liquid phase. The nitrating mixture was prepared by mixing nitric acid in concentrated sulfuric acid maintained at 0° C. in a v/v~40/60.

Nitration of Acetophenone
The batch method for nitration of acetophenone was followed as in Org. Syn. Coll. Vol. 2, 434 (1943).

Example 2

Reduction of m-Nitro Acetophenone

Continuous Flow Experiments:
The reaction was carried out in a SS316 of ⅛" OD tube of volume 8.5 ml with 1 gm m-nitroacetophenone in 20 ml methanol and 5 gm $SnCl_2.2H_2O$ in 20 ml 10% HCl pumped using syringe pumps with a residence Time=22 min at 100° C. The reaction was seen to be complete with only the product being observed at the outlet.

Example 3

Nitration of Acetophenone

The mixing of acetophenone in sulfuric acid was carried out in batch manner at very low temperature (−11° C.). The mixing was seen to be extremely exothermic and the heat generation rate during the rapid temperature rise was 3.9° C./ml, which would limit the mixing volumes.

Continuous Flow Experiments
Experiments were carried out using a ⅛" tube at 5° C. At residence time of 5 min, 79% yield of the meta product was obtained. Longer residence time reduced the yield of the desired isomer and yielded many impurities.

With the experimental set-up as shown in FIG. 2, and using a ⅛" tubular reactor at 10° C. and 10 min residence time the yield of the meta isomer was 23% and 67% with 10 and 20 volume equivalents of the nitrating mixture, respectively.

With the experimental set-up as shown in FIG. 2, and using a ⅛" tubular reactor at 10 min residence time the yield of the meta isomer was 60%, 66% and 63% at 0° C., 5° C. and 10° C., respectively.

Based on these observations, the optimized conditions for the reaction were 5° C., 5 minutes residence time, w/v ratio of acetophenone to sulfuric acid of 1:2.5, v/v ratio of substrate mixture to nitrating mixture of 1:1.66 (with standard nitrating mixture), that yields 98.55% of the expected yield of the desired meta isomer. The product composition contains ortho-o:meta~17:81.

Example 4

Nitration of Acetophenone with Fuming Nitric Acid Continuous Flow Process

The experimental setup consisted of two pumps, a constant temperature bath and a Micromixer, as shown in FIG. 2. Neat acetophenone and fuming nitric acid (98%) were taken in SS316 syringes. For the continuous flow experiments, tubular reactor of ⅛" SS316 tube was used. In all the cases, flow rates were adjusted to achieve the desired residence time. T-mixer and AMaR1 micromixer was used for the mixing of reactants. At −10 C, with 6 minutes residence time, 95.5% conversion was observed with 2.21:1 mole ratio of the meta to ortho nitro acetophenone.

Example 5

Nitration of Acetophenone with Fuming Nitric Acid Continuous Flow Process

For the experimental setup and procedure mentioned in Example (4), at 10° C., with 10 minutes residence time, 93% conversion was observed with 1.83:1 mole ratio of the meta to ortho nitro acetophenone.

Example 6

Nitration of Acetophenone with Fuming Nitric Acid Continuous Flow Process

For the experimental setup and procedure mentioned in Example (4), at 10° C., with 16 minutes residence time, 99.7% conversion was observed with mole ratio of the meta to ortho nitro acetophenone 1.62:1.

Example 7

Nitration of Acetophenone with Fuming Nitric Acid Continuous Flow Process

For the experimental setup and procedure mentioned in Example (4), at 0° C., with 20 minutes residence time, 97.6% conversion was observed with mole ratio of the meta to ortho nitro acetophenone~1.43:1.

Example 8

Reduction of m-Nitro Acetophenone

Batch Experiment

The experiments in batch operation with 2 gm m-nitro acetophenone, 4 gm granulated tin metal, 40 ml 10% HCl, 24 ml of 40% NaOH (used for work-up) at 85 to 95° C. in 2 hrs yielded 74% of the meta amino acetophenone (M. P.~96-97° C.). The product was confirmed by NMR. Tin was found to be insoluble in 10% HCl at 85° C., however it was soluble in presence of substrate and the reaction mixture became homogeneous within 45 min. The reaction was conducted by following the above dissolution procedure and sample was taken after 24 hours. The solution was in slurry form with some amount of undissolved tin. The experiment was repeated and six samples were taken with 15 min interval after the solution became homogeneous. The samples were quenched with 40% NaOH and then extracted by ether and the analysis showed that all the samples contained only the product. Additional experiments were carried out using 1.9 gm of the catalyst $SnCl_2.2H_2O$, methanol and 10% HCl. The reaction was kept for reflux at 78° C. for 4 hrs and the reaction was still incomplete. Hence with higher catalyst quantity (3.87 gm) and reflux at 110° C. yielded 95% conversion in 30 min.

Continuous Flow Experiment

In the continuous flow reduction of m-nitro acetophenone, the experimental set-up consisted of two pumps and a thermostat. Experiments were carried out at 100° C. in a 1/16" o.d. tube having 8.5 ml volume. Experiments yielded 100% of the expected product in 22 min residence time.

Example 9

The reduction reaction of meta nitro acetophenone was carried out in a SS316 of 1/8" OD tube of volume 8.5 ml with 1 gm m-nitroacetophenone in 20 ml methanol and 5 gm $SnCl_2.2H_2O$ in 20 ml 10% HCl pumped using syringe pumps with a residence Time=22 min at 100° C. The reaction was seen to be complete with only the product being observed at the outlet.

Example 10

Continuous flow reduction of m-nitro acetophenone was carried out in a silicone tube (4.4 ml volume, 1.5 mm i.d.) at 100° C. yielded 70% yield of the product. The reaction was further optimized to yield 100% yield in 5 min.

Advantage of the Present Invention

According to the continuous flow nitration and subsequent reduction of acetophenone, the desired product yield/quality of the products at both the stages are higher than the batch operation. Flow synthesis yields a safer process.

We claim:

1. A continuous method of conversion of acetophenones to amino substituted acetophenones using tubular reactor, said method comprising the steps of:
   (a) nitration of acetophenone with nitration mixture at 0-10° C. or with fuming nitric acid at −10-20° C. to obtain nitro acetophenone;
   (b) isolating the m-nitro acetophenone from a mixture of o- and m-nitro acetophenone by quenching of the reaction in ice and extraction in an organic solvent; and
   (c) reduction of the m-nitro acetophenone with a reducing agent to obtain m-amino acetophenone, wherein the method provides an uniform output of product, wherein residence time in the tubular reactor is about 5 to 22 minutes, and
wherein the selectivity towards m-nitro acetophenone is in the range of 93 to 100% and the selectivity towards m-amino acetophenone is in the range of 95 to 100%.

2. The continuous method of conversion of acetophenones to amino substituted acetophenones using tubular reactor according to claim 1, wherein the acetophenone is dissolved in sulfuric acid prior to subjecting to nitration process.

3. The continuous method of conversion of acetophenones to amino substituted acetophenones using tubular reactor according to claim 2, wherein the ratio of acetophenone to sulfuric acid ranges from 1:0 to 1:2.5 w/v.

4. The continuous method of conversion of acetophenones to amino substituted acetophenones using tubular reactor according to claim 1, wherein the ratio of acetophenon to nitrating mixture is 1:1.66 v/v.

5. The continuous method of conversion of acetophenones to amino substituted acetophenones using tubular reactor according to claim 1, wherein reducing agent is selected from the group consisting of $SnCl_2$ and $Na_2S$.

6. The continuous method of conversion of acetophenones to amino substituted acetophenones using tubular reactor according to claim 1, wherein organic solvent is selected from the group consisting of toluene and diethyl ether.

7. The continuous method of conversion of acetophenones to amino substituted acetophenones using tubular reactor according to claim 1, wherein the nitration mixture is standard nitrating mixture.

* * * * *